United States Patent [19]

Petersen et al.

[11] Patent Number: 5,192,405
[45] Date of Patent: Mar. 9, 1993

[54] PROCESS FOR EFFECTING HIGH EFFICIENCY SEPARATIONS BY CAPILLARY ELECTROPHORESIS

[75] Inventors: John S. Petersen, Acton; Michael Merion, Upton, both of Mass.

[73] Assignee: Millipore Corporation, Bedford, Mass.

[21] Appl. No.: 756,718

[22] Filed: Sep. 9, 1991

Related U.S. Application Data

[63] Continuation of Ser. No. 640,177, Jan. 11, 1991, abandoned.

[51] Int. Cl.$^5$ .................. G01N 27/26; B01D 57/02
[52] U.S. Cl. ........................ 204/180.1; 204/299 R
[58] Field of Search .......................... 204/180.1

[56] References Cited

U.S. PATENT DOCUMENTS 4,675,300 6/1987 Zare ................................. 356/318

OTHER PUBLICATIONS

"Capillary Electrophoresis of Proteins in Buffers containing High Concentrations of Zwitterionic Salts", J. Chromatography, 480 (1989) 301-310, Bushey.

Swedberg, "Use of non-ionic and zwitterionic surfactants to enhance selectivity in high performance capillary Electrophoresis", J. Chromatography, 503 (1990) 449-452.

*Primary Examiner*—John Niebling
*Assistant Examiner*—John S. Starsiak, Jr.
*Attorney, Agent, or Firm*—Paul J. Cook; Andrew T. Karnakis

[57] ABSTRACT

Capillary electrophoresis is effected by introducing into a capillary a buffer solution a zwitterion composition comprised of substantially equal numbers of positive and negative charges when the negative charges are desired from sulfonate or sulfate groups and the positive charges are derived from quaternary amines, quaternary phosphines or quanternary arsines. A sample is introduced into the capillary and an electric field is established through the capillary to cause the sample to migrate through the capillary.

16 Claims, 9 Drawing Sheets

PROCESS FOR EFFECTING HIGH EFFICIENCY SEPARATIONS BY CAPILLARY ELECTROPHORESIS

This is a continuation of copending application(s) Ser. No. 07/640,177 filed on Jan. 11, 1991, now abandoned.

FIELD OF THE INVENTION

The present invention relates to novel zwitterions and to a process for modifying solid surfaces exposed to macromolecules, especially proteins. More particularly this invention relates to novel zwitterions and to the buffer solutions containing zwitterions used to modify solid surfaces in electrophoretic separations by capillary electrophoresis.

Capillary electrophoresis(CE) is an efficient analytical separation technique for the analysis of minute amounts of sample. CE separations are performed in a narrow diameter capillary tube, which is filled with an electrically conductive medium termed the "carrier electrolyte". An electric field is applied between the two ends of the capillary tube, and species in the sample move from one electrode toward the other electrode at a rate which is dependent on the electrophoretic mobility of each species as well as on the rate of bulk fluid movement in the tube. CE may be performed using gels or liquids in the capillary. In one liquid mode, known as capillary zone electrophoresis (CZE), separations are based on differences in the free solution mobility of sample species. In another liquid mode, micelles are used to effect separations based on differences in hydrophobicity. This is known as Micellar Electrokinetic Capillary Chromatography. In capillary gel electrophoresis the capillary tube is filled with an electrically conductive gel rather that with liquid electrolyte. The gel functions as an anticonvective medium and minimizes sample band spreading. In CZE, a high molecular weight solute such as a polyethylene oxide or hydroxymethyl cellulose can be added to the solvent to provide sieving effects analagous to those supplied by a gel.

CE is advantageous for several reasons. These include short separation times, high resolution and small sample size. For example, separation speeds using CE can be 10 to 20 times faster than conventional gel electrophoresis. In part, high resolution can be obtained through the use of high voltages because of the rapid dissipation of heat by the capillary. Further, band broadening due to convection is minimized due to the narrow capillary inner diameter. In electrophoresis, the phenomenon of electroosmosis, or electroosmotic flow (EOF) occurs. This is a bulk flow of liquid which can move in either direction within the capillary tube and which affects all of the sample molecules regardless of charge. EOF can contribute to separation speed in free zone CE. CE in small capillaries (less than or equal to 100 um) has proven useful as a method of separating small molecules and, under certain special conditions (pH less than 3 or pH greater than 9), has been useful for macromolecule and protein separations. The conditions under which protein analysis can be successfully conducted depend on the isoelectric point (pI) of the proteins being analyzed and the tendency of proteins to adsorb to the capillary surface. It is desirable to reduce protein adsorption on the capillary surface since it interferes with the desired protein separation within the capillary. Jorgenson et al, Science, 222 (1983) page 266 have noted that attempts to separate cytochrome C, lysozyme and ribonuclease A, in untreated fused silica capillaries with a phosphate buffer at pH 7 were accompanied by strong tailing and suggested this might be caused by Coulombic interactions of the positively charged proteins and the negatively charged capillary wall. This coulombic interaction can be decreased through the use of buffers with high salt concentrations; $K_2SO_4$ in particular is effective for this purpose (as shown by) Green and Jorgenson, J. Chromatogr., 478 (1989) 63. However, the high conductivity of these buffer solutions limits the applied potential to 5 kV even when a relatively narrow 25 $\mu$m capillary is used to allow adequate heat dissipation. The result of the use of relatively low voltage is long analysis times, e.g., 60 minutes.

Subsequently, Bushey and Jorgenson, J. Chromatog. 480 (1989) 301–310 attempted to use amino acids or amino acid derivatives to eliminate the need for potassium sulfate. However, they were unable to obtain high efficiencies without adding some $K_2SO_4$ to the solution and were still limited to 25 $\mu$m capillaries. An additional disadvantage of some of the amino acid derivatives Jorgenson examined is the strong UV absorbance of these compounds at short wavelengths (220 nm) since this absorbance causes interference with the detectors used in conjunction with the CE process.

Efficiency of separation in CE can be reported as the number of theoretical plates (N) calculated from measurements of the migration time (retention time) and peak width of a compound of interest. For the purpose herein, column efficiencies are reported in terms of plates at half height where N is equal to 5.54 times the square of the retention time divided by the square of the peak width at half height.

Since the efficiency of the separation process is Proportional to the field strength (see Wallingford and Ewing, Adv, Chromatogr. 29 (1989) pp. 5–8), it is desirable to operate at the highest possible field strength. Field strength is ultimately limited by the ability of the capillary to dissipate heat and the amount of heat generated by the buffer system. While smaller capillaries dissipate heat more efficiently, increasing the diameter of the capillary in the CE process increases the size of the on column detector cells and the detector concentration sensitivity. Thus, it is desirable to minimize the heat generated by the buffer system which is equivalent to minimizing the conductivity of the buffer.

SUMMARY OF THE INVENTION

The present invention provides amino sulfonate, amino sulfate and novel phosphonium sulfonate zwitterions which are useful in CE for the high efficiency separations of macromolecules such as proteins, peptides, nucleic acids, carbohydrates, synthetic polymers or the like. In contrast to the amino acid zwitterions utilized in the CE process of the prior art, the buffer to which the zwitterion is added in this invention does not require the use of added salts such as potassium sulfate to effect the separation. In addition, the buffer solutions containing the zwitterions of this invention are characterized by a relatively low conductivity so that the buffer solution is useful at high field strength, e.g., 200–300 V/cm and in relatively large capillaries having a diameter up to about 100 microns. The CE process of this invention can be effected under conditions which maintain EOF within the capillary. The CE process of this invention while limiting UV absorbance by the buffer so that detection can be effected at wavelengths as low as 185 nm. In addition, the present invention can be conducted without the need for an internal coating within the capillary.

DESCRIPTION OF SPECIFIC EMBODIMENTS

This invention provides a process for effecting electrophoretic separation of molecules in a capillary, which comprises introducing into the capillary a buffer solution containing a zwitterion or zwitterions comprised of substantially equal numbers of positive and negative charges where the negative charge or charges are derived from sul- fonate or sulfate groups and the positive charge or charges are derived from quaternary amines, quaternary phosphines or quaternary arsines. The sample then is introduced into the capillary and an electrical field is established through said capillary to cause the sample to migrate through the capillary. In the monomeric zwitterions used in this invention, the negative and positive charges are equal. In the polymeric zwitterions used in this invention, the number of positive and negative charges are substantially equal. The term "substantially equal" as used herein and referring to these charges means equal or only slightly different. Where the numbers of positive and negative charges are slightly different, the difference arises from charges associated with polymer initiation or termination or with partial hydrolysis of the polymer resulting in the formation of charged groups. The monomers from which the polymers are made do contain equal numbers of positive and negative charges.

Representative suitable zwitterions are described by one of the following formulas:

$RR^1R^2N^+(CH_2)_xY^-$     Formula I
$RR^1R^2P^+(CH_2)_xY^-$     Formula II and mixtures thereof wherein x, y and z can be the same or different and are integers from 1 to 30 (in the case of formula V, x can range from 1 to 10,000); R, R1, R2, R3, R4, and R5 can be the same or different and are hydrogen, alkyl groups containing from 1 to 30 carbon atoms, two R groups bonded to the same nitrogen as part of a cyclic structure (e.g., pyrrolidine or morpholine) or hydroxyalkyl groups containing from 1 to 30 carbons. Y can be the same or different and is either sulfate or sulfonate. Preferred zwitterions include: $(HOCH_2CH_3)_3N(CH_2)_3SO_3$, $Me_3N(CH_2)_3SO_3$, $Et_3N(CH_2)_3SO_3$, $n-Pr_3N(CH_2)_3SO_3$, $CH_3(CH_2)_{11}Me_2N(CH_2)_3SO_3$, $CH_3(CH_2)_{13}Me_2N(CH_2)_3SO_3$, $CH_3(CH_2)_{15}Me_2N(CH_2)_3SO_3$, $CH_3(CH_2)_{17}Me_2N(CH_2)_3SO_3$, $Me_3P(CH_2)_3SO_3$, and $O_3S(CH_2)_3Me_2N(CH_2)_6NMe_2(CH_2)_3SO_3$. Me is methyl. Et is ethyl. N-Pr is normal propyl.

The zwitterions of this invention can be utilized in the process of this present invention either alone or in admixture. The zwitterions of this invention are utilized in admixture with the buffer solution of a capillary electrophoresis process. Any conventional buffer can be utilized such as phosphate, borate, acetate, citrate or aminosulfonate. The zwitterions are utilized at a concentration between about $10^{-7}M$ and about 3.0M. The zwitterions function to interact with the charged internal surface of the capillary and to screen the surface charges so that little or no charged interaction occurs between the surface and the macromolecule being separated.

It is preferred to utilize the sulfonate form of the zwitterions of this invention since there is a reduced tendency for it to hydrolyze as compared with the sulfate ion. In addition, it is preferred to utilize zwitterions wherein x, y and z are integers from 1 to 4 since these compounds are more soluble than the zwitterions having longer carbon chains.

In use, the zwitterions or mixtures of the zwitterions of this invention are mixed with a buffer solution which then is introduced into the capillary tube of a CE apparatus. Each end of the tube is positioned in electrical contact with an electrode after a volume of sample is introduced into the inlet of the capillary. A high voltage, usually between about 100 and 200 V/cm is applied across the electrodes at the capillary inlet and at the capillary outlet. The sample molecules migrate through the capillary tube under the influence of the electric field created by the voltage applied to the electrodes. The molecules in the sample are separated from each other and are analyzed on line by a conventional detector such as a UV absorbance detector. The sample then exits the capillary tube downstream of the detector.

The following examples illustrate the present invention and are not intended to limit the same.

EXAMPLE 1

Figure 1:
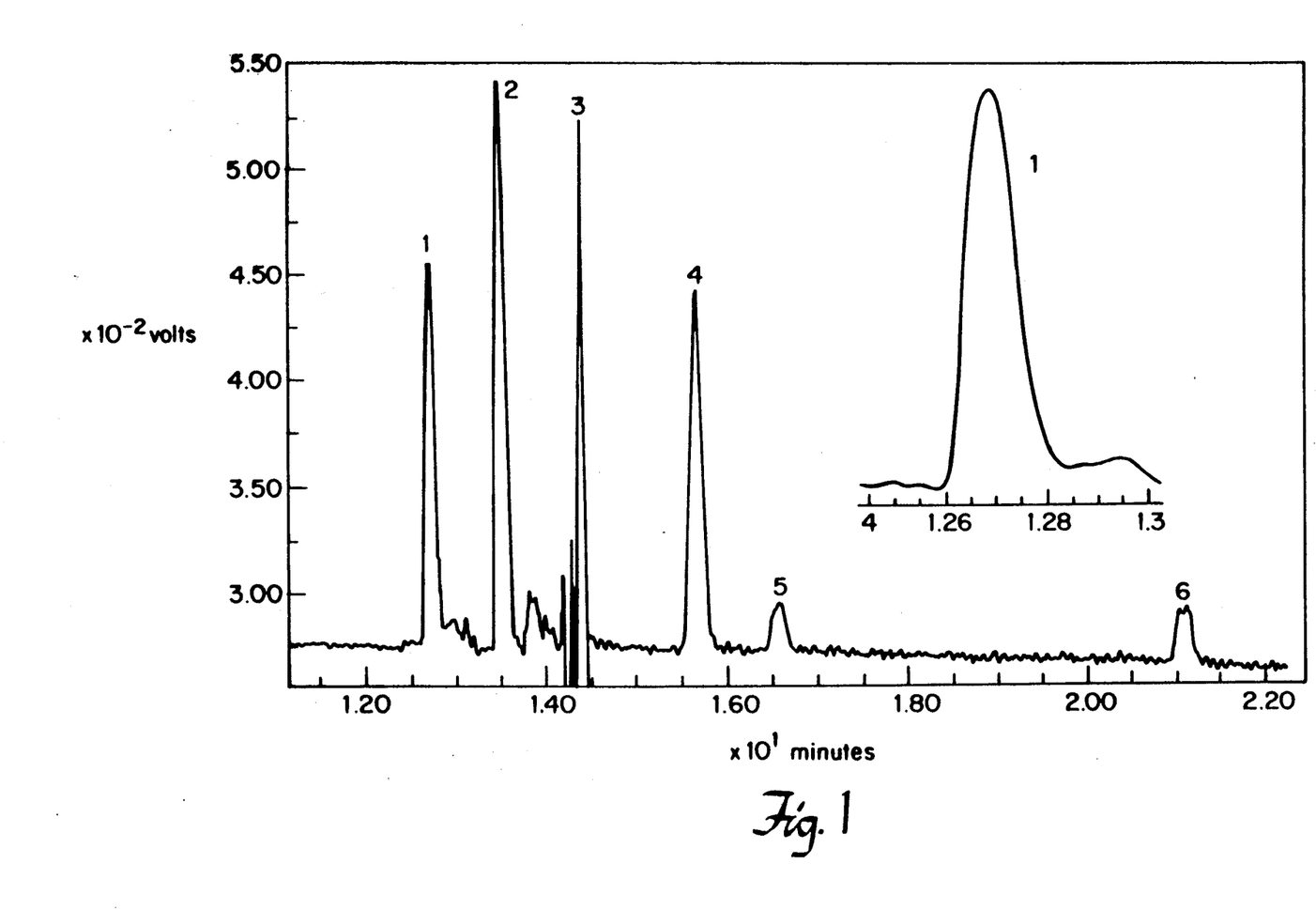
FIG. 1 is an electropherogram of a mixture of lysozyme, cytochrome C, carbonic anhydrase and beta lactoglobulin run at pH 7 in a solution of phosphate buffer and triethylammoniumpropylsulfonate of Example 1.

A 60 cm fused silica capillary of 50 μm I.D. externally coated with polyimide (Polymicro Technologies) was freshly cut from a roll and approximately 1 cm section of polyimide coating was removed 7.5 cm from one end. The capillary was installed in a Waters Quanta 4000 with a positive power supply (cathode at detector end of capillary). The capillary was flushed with 0.5M KOH for 5 minutes, followed by distilled water. A buffer solution was prepared by adding triethylammoniumpropylsulfonate 5.5 g to a 200 mM solution of sodium phosphate at pH 7.0 and bringing the volume to 25 ml such that the final phosphate concentration was 100 mM and the zwitterion 1M. The pH was unchanged by the addition of the zwitterion. This buffer was placed in reservoirs at the capillary inlet and outlet and the capillary was filled with the buffer. A sample containing lysozyme 100 μg/mL, cytochrome C 100 μg/mL, carbonic anhydrase 100 μg/mL, beta lactoglobulin 10 μg/mL and methyl red in water was prepared. The sample was introduced into the capillary (30 sec hydrostatic injection) and the electrophoretic run conducted at 15 kV (current 60 μamp). Detection was performed at 185 nm. FIG. 1 illustrates the excellent separation obtained and the high efficiency of the system (72K plates for lysozyme). Peak 1 is lysozome. Peak 2 is cytochrome C. Peak 3 is a neutral marker. Peak 4 is carbonic anhydrase. Peak 5 is B lactoglobulin. Peak 6 is methyl red.

EXAMPLE 2

Figure 2:
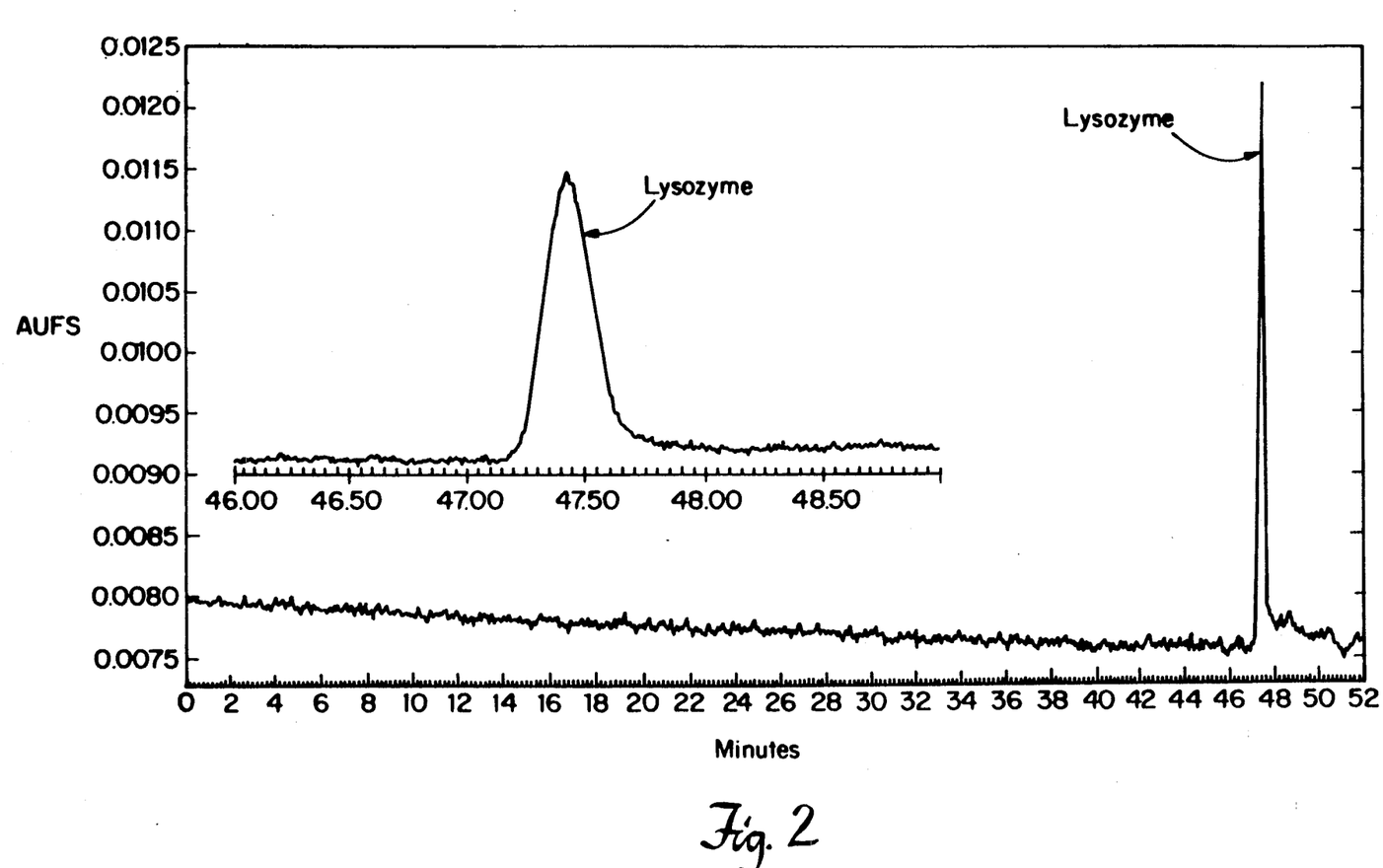
FIG. 2 is an electropherogram of a mixture of lysozyme and cytochrome C, run at pH 7 in a solution of phosphate buffer and tripropylammoniumpropylsulfonate of Example 2.

This experiment differs from example 1 in that a 75 μm capillary was used and detection was performed at 214 nm. The buffer was 200 mM phosphate, pH 7.0 containing 1M tri-n- propylammoniumpropylsulfonate. The voltage was 10 kV giving a current of 75 μA. Using a smaller injected volume, 250,000 plates were obtained for lysozyme as shown in FIG. 2.

EXAMPLE 3

Figure 3:
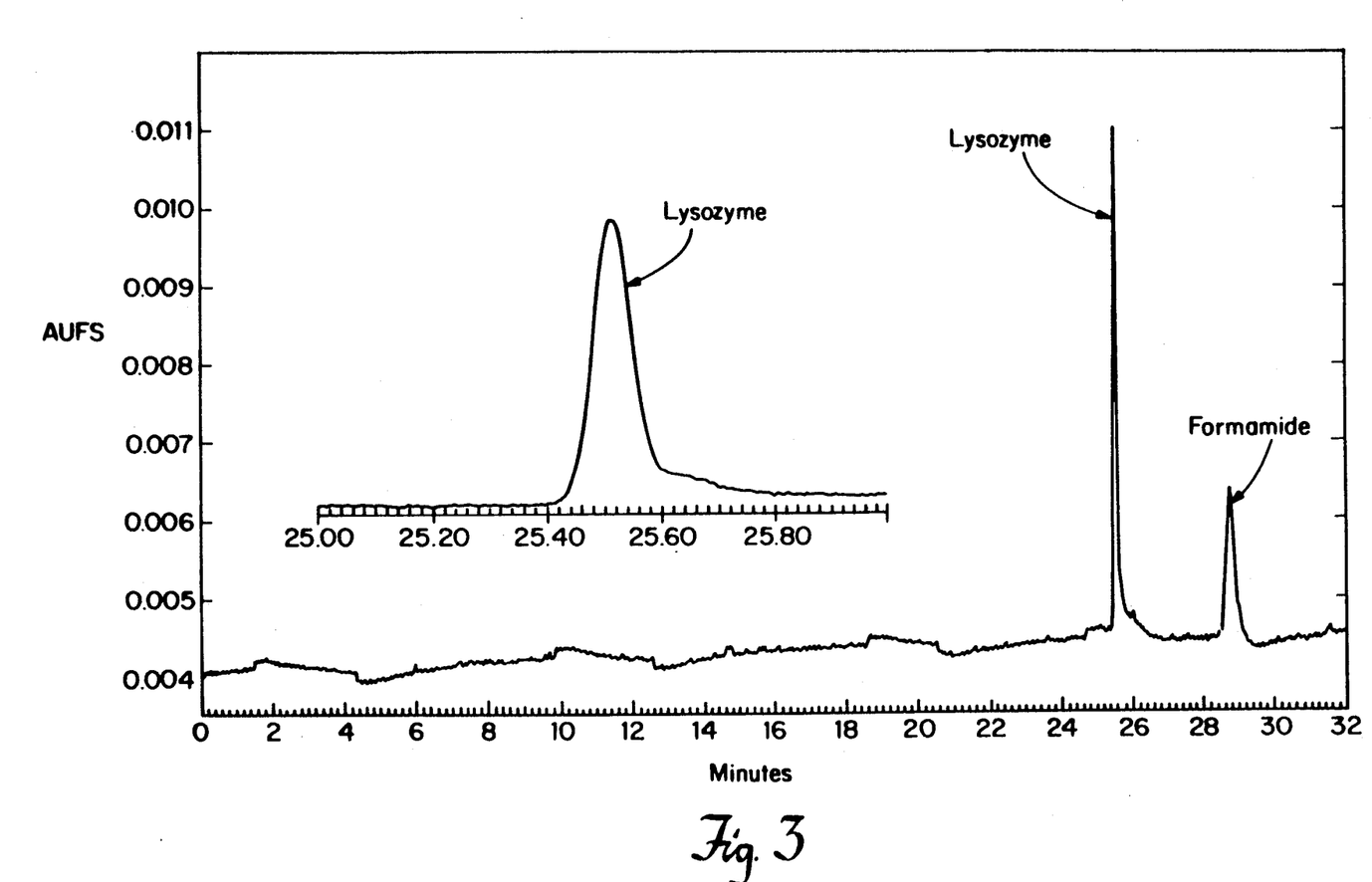
FIG. 3 is an electropherogram of lysozyme and formamide run at pH 7 in a solution of phosphate buffer and trimethylammoniumpropylsulfonate of Example 3.

This experiment differs from example 2 in that the zwitterion was trimethylammoniumsulfonate, the concentration was 1.5M and a smaller injection (2 second hydrostatic was used). Using a voltage of 7 kV a current of 82 μA was observed and about 700,000 plates were obtained for the lysozyme peak as shown in FIG. 3.

EXAMPLE 4

Figure 4:
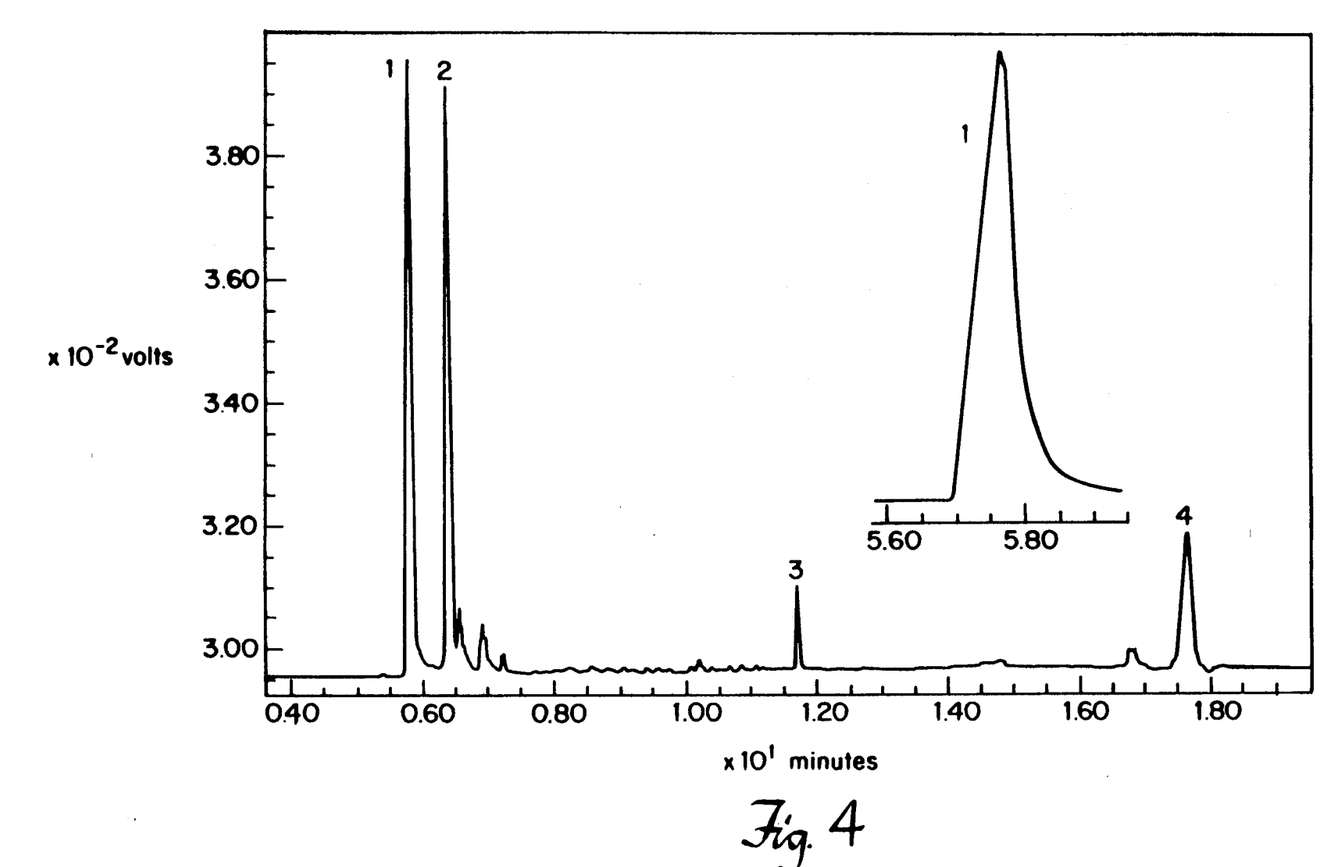
FIG. 4 is an electropherogram of a mixture of lysozyme, cytochrome C and carbonic anhydrase, run at pH 4.4 in a solution of phosphate buffer and triethylammoniumpropylsulfonate of Example 4.

The same apparatus was used as in Example 1 except that detection was at 214 nm. The running buffer was 100 mM sodium phosphate at pH 4.4 containing 1M triethylammoniumpropylsulfonate. The electrophoresis was conducted at 30 kV and a current of 60 μA was observed. Excellent efficiencies were observed for all proteins as shown in FIG. 4. Peak 1 is lysozyme. Peak 2 is cytochrome C. Peak 3 is carbonic anyhdrase. Peak 4 is methyl red.

EXAMPLE 5

Figure 5:
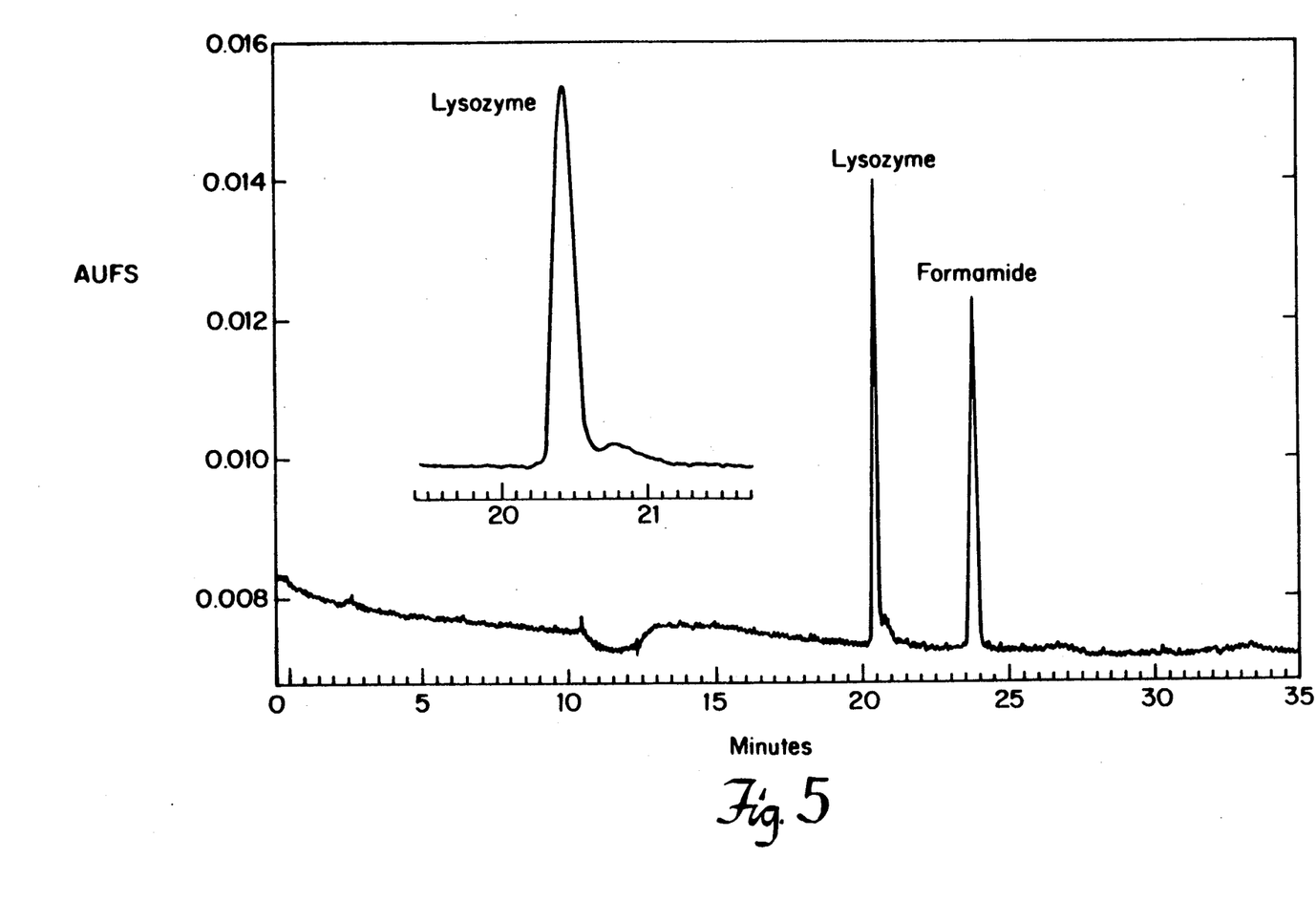
FIG. 5 is an electropherogram of lysozyme and formamide run at pH 7 in a solution of phosphate buffer and the biszwitterion of Example 5.
Figure 6:
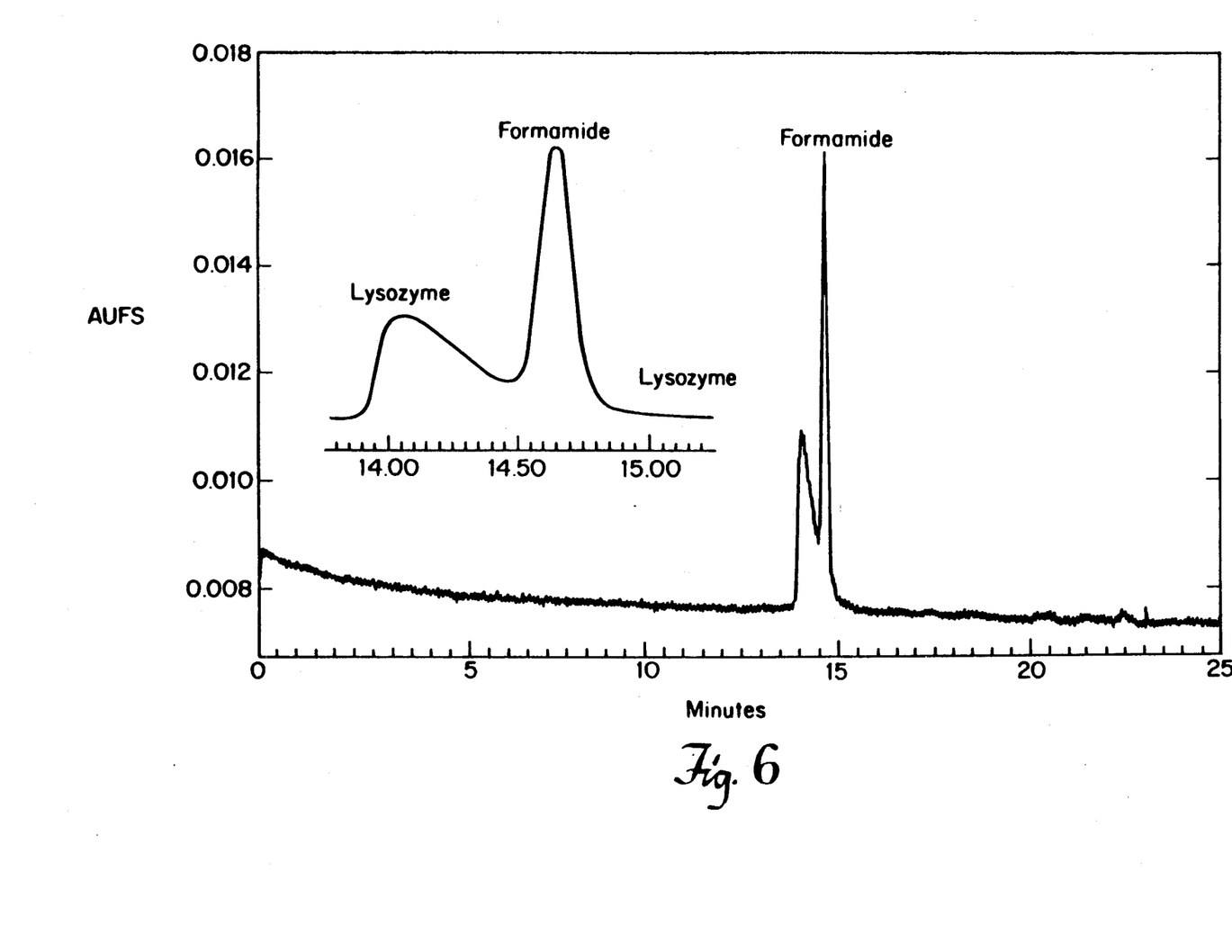
FIG. 6 is an electropherogram of the same sample as in FIG. 5 in pH 7 buffer without the zwitterion.

This experiment differs from example 2 in that the phosphate concentration was 120 mM and a bis-zwitterion, N, N'-bis(sulfopropyl)-N,N,N',N'tetramethyl-1,6 hexanediamine, was used. The zwitterion concentration was 0.5M. Using a voltage of 8 kV a current of 62 uA was observed and 87,000 plates were obtained for the lysozyme peak, FIG. 5. Without the zwitterion, lysozyme elutes as a broad tailing peak as shown in FIG. 6.

EXAMPLE 6

Figure 7:
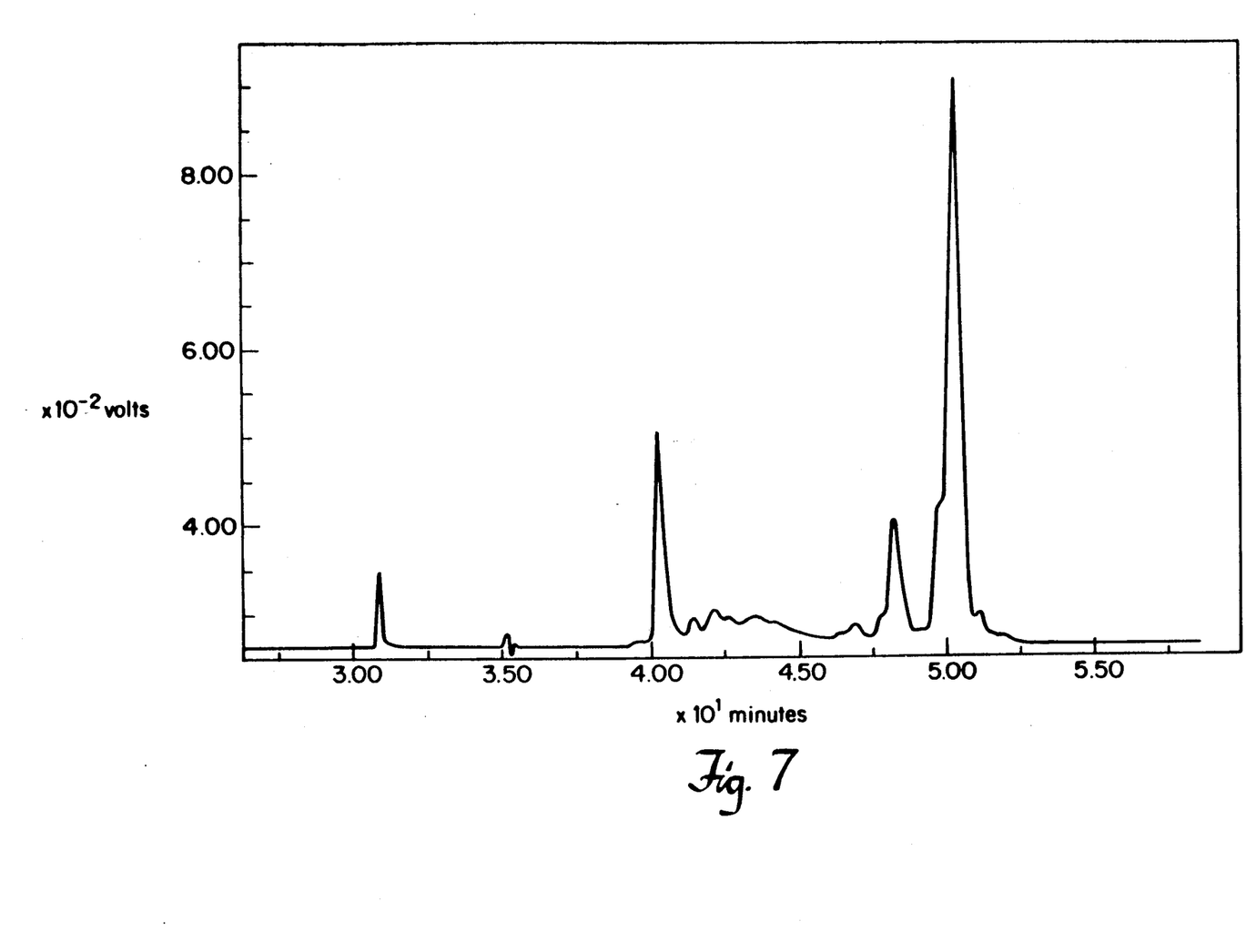
FIG. 7 is an electropherogram of egg white run at pH 7.0 in a solution of phosphate buffer and triethylammoniumpropylsulfonate of Example 6.

A. The same apparatus was used as in Example 1 except that a 75 μm capillary was used with detection at 214 nm. The running buffer was 180 mM sodium phosphate with 1.8M triethylammoniumpropylsulfonate. The analysis was performed at a voltage of 10 kV which generated a current of 40 μA. The sample was a 5% solution of egg white in the running buffer as shown in FIG. 7.

Figure 8:
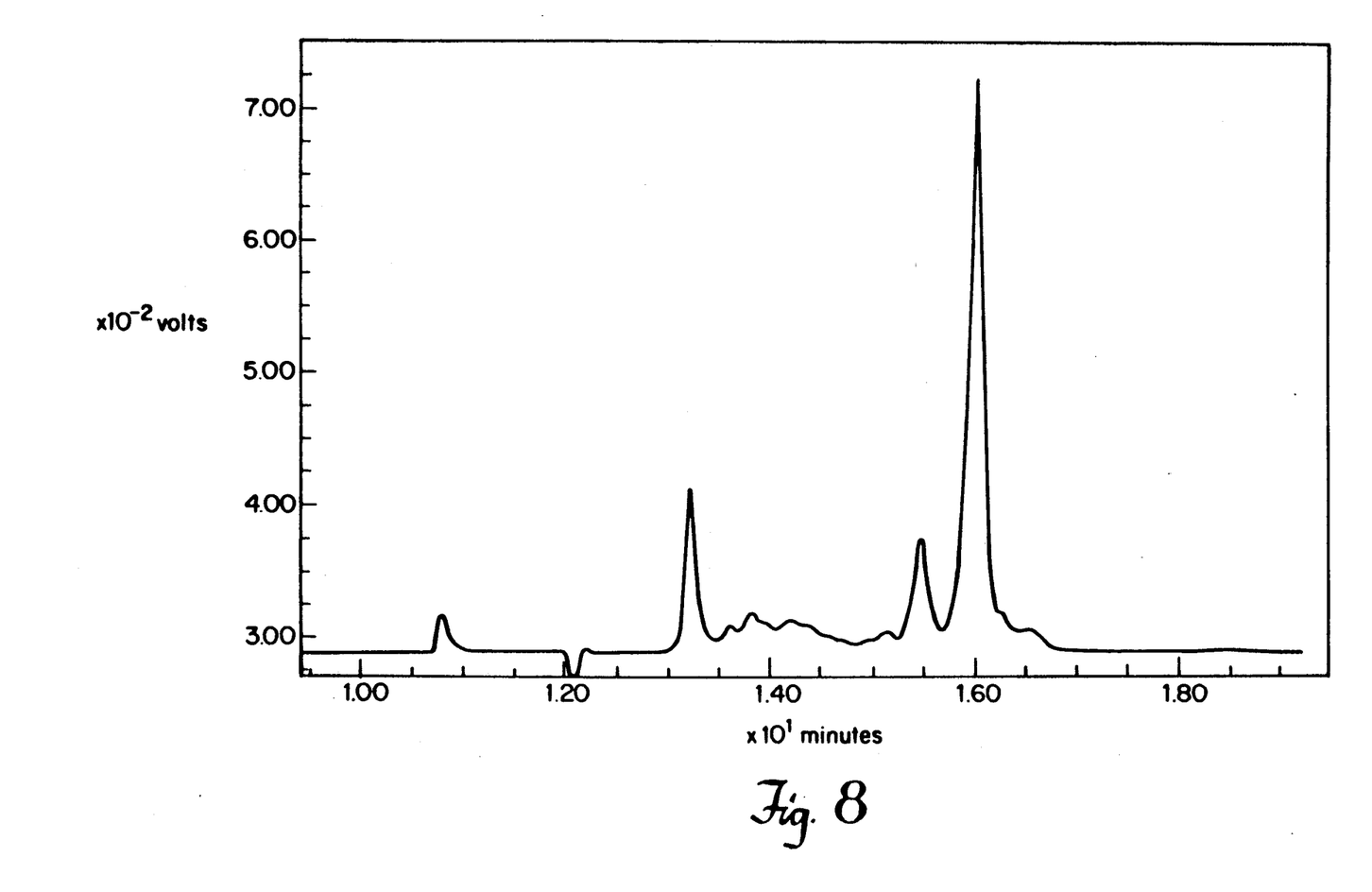
FIG. 8 is an electropherogram of the same sample as FIG. 7 using the trimethylammoniumpropylsulfonate zwitterion in place of the triethyl compound.

B. Conditions were the same as A except the buffer was 100 mM sodium phosphate containing 1.0M trimethylammoniumpropylsufonate. The 10 kV applied gave a current of 78 μA and give the results shown in FIG. 8.

EXAMPLE 7

Synthesis of trimethylphosphoniumpropylsulfonate

A solution of 1,3-propanesultone (36.0 g) was added dropwise to a mechanically stirred solution of trimethylphosphine (24.7 g) in acetonitrile (350 mL) under a nitrogen atmosphere. The internal temperature was maintained between 5° and 10° C. with an ice bath. The addition was complete in 1.5 hours. The solution was stirred for 18 hours during which time it was allowed to warm to room temperature. The product, a white crystalline solid, was recovered by filtration and washed with acetonitrile (3×350 mL). The salt was dried (30° C., 28 in Hg, 16 h). The 1H NMR was consistent with the structure of trimethylphosphoniumpropylsulfonate.

Use of trimethylphosphoniumpropylsulfonate

Figure 9:
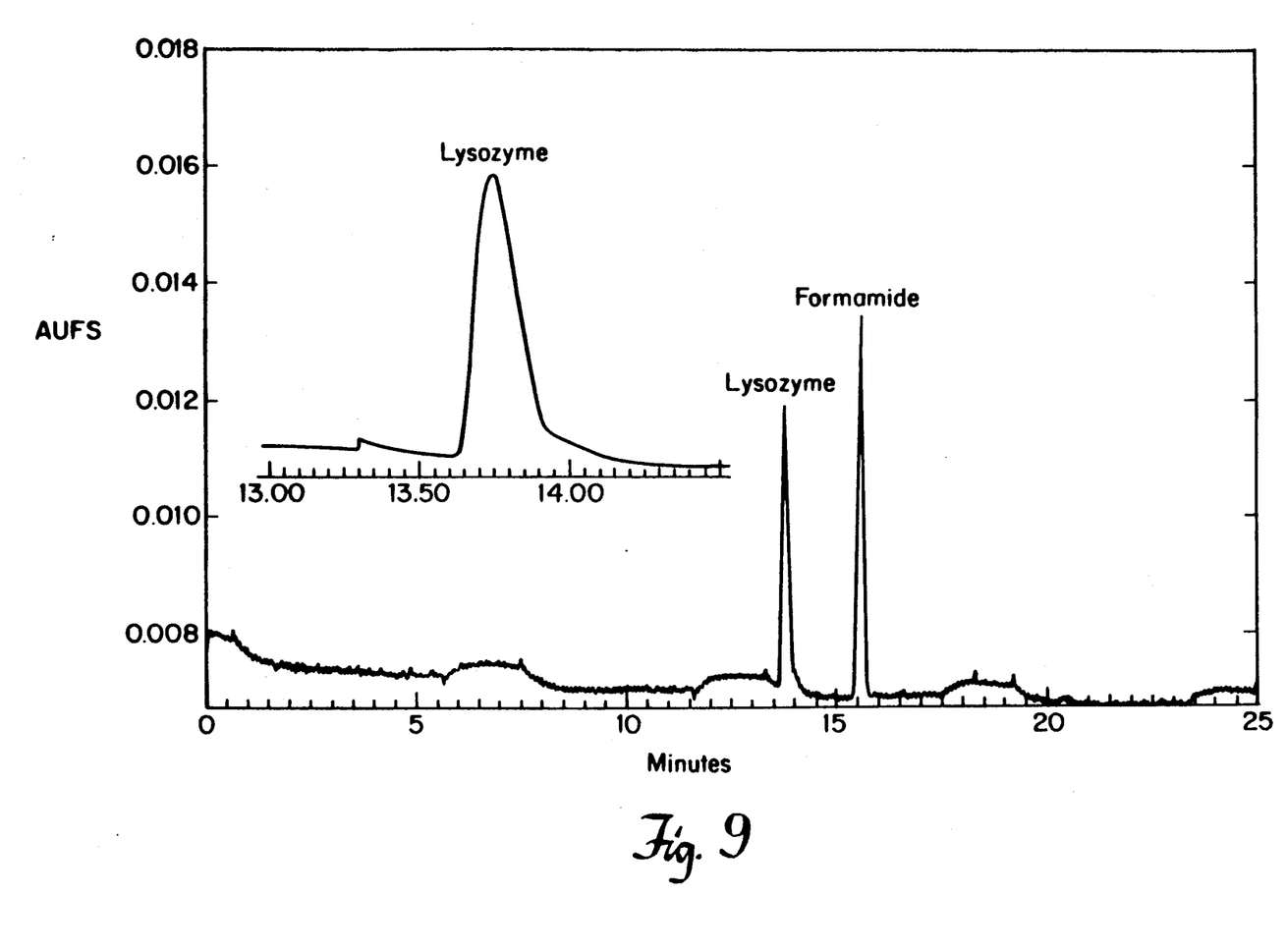
FIG. 9 is an electropherogram of lysozyme and formamide run at pH 7 in a solution of phosphate buffer and the trimethylphosphoniumpropylsulfonate of Example 7.

The same apparatus was used as in Example 1 except that a 75 μm capillary was used with detection at 214 nm. The running buffer was 120 mM phosphate containing 1M trimethyl-phosphoniumpropylsulfonate at pH 7.0. With a voltage of 8 kV a current of 69 μA was observed and 37,000 plates were obtained for lysozyme as shown in FIG. 9.

What is claimed is:

1. The process for effecting electrophoretic separation of molecules in a sample within a capillary which comprises:

introducing into said capillary a buffer solution containing at least one zwitterion comprised of substantially equal numbers of positive and negative charges and having the formula selected from the group consisting of:

$$RR^1R^2N^+(CH_2)_xY^- \quad \text{Formula I}$$
$$RR^1R^2P^+(CH_2)_xY^- \quad \text{Formula II}$$

$$-Y(CH_2)_x\overset{\overset{R}{|}}{N^+}(CH_2)_y\overset{\overset{R^2}{|}}{N^+}(CH_2)_zY^- \quad \text{Formula III}$$
$$\phantom{-Y(CH_2)_x}\underset{R^1}{|}\phantom{(CH_2)_y}\underset{R^3}{|}$$

Formula IV and mixtures thereof wherein x, y and z can be the same or different and are integers from 1 to 30; R, $R^1$, $R^2$, $R^3$, $R^4$ and $R^5$ can be the same or different and are hydrogen, alkyl groups containing from 1 to 30 carbon atoms, two R groups bonded to the same nitrogen as part of a cyclic structure or hydroxyalkyl groups containing from 1 to 30 carbons: Y can be the same or different and is sulfate or sulfonate, introducing said sample into said capillary and establishing an electrical field through said capillary to cause the sample to migrate through said capillary and detecting the separated analytes.

2. The process of claim 1 wherein the negative charges are sulfonate.

3. The process of claim 1 wherein the negative charges are sulfate.

4. The process of claim 1 wherein x, y and z are integers from 1 to 4.

5. The process of claim 1 wherein the zwitterion is $Me_3N(CH_2)_3SO_3$.

6. The process of claim 1 wherein the zwitterion is $Et_3N(CH_2)_3SO_3$.

7. The process of claim 1 wherein the zwitterion is $n\text{-}Pr_3N(CH_2)_3SO_3$.

8. The process of claim 1 wherein the zwitterion is $(HOCH_2CH_2)_3N(CH_2)_3SO_3$.

9. The process of claim 1 wherein the zwitterion is $CH_3(CH_2)_{11}Me_2N(CH_2)_3SO_3$.

10. The process of claim 1 wherein the zwitterion is $CH_3(CH_2)_{13}Me_2N(CH_2)_3SO_3$.

11. The process of claim 1 wherein the zwitterion is $CH_3(CH_2)_{15}Me_2N(CH_2)_3SO_3$, 12. The process of claim 1 wherein the zwitterion is $CH_3(CH_2)_{17}Me_2N(CH_2)_3SO_3$.

13. The process of claim 1 wherein the zwitterion is $Me_3P(CH_2)_3SO_3$.

14. The process of claim 1 wherein the zwitterion is $O_3S(CH_2)_3Me_2N(CH_2)_6NMe_2(CH_2)_3SO_3$.

15. The process of claim 1 wherein the zwitterion has the formula:

Formula II.

16. The process for effecting electrophoretic separation of molecules in a sample with a capillary which comprises:
introducing into said capillary a buffer solution containing at least one zwitterion comprised of substantially equal numbers of positive and negative charges and having the formula:

Formula V and mixtures thereof wherein y and z can be the same or different and are integers from 1 to 30; R, $R^1$, $R^2$, $R^3$, $R^4$ and $R^5$ are the same or different and are hydrogen, alkyl groups containing from 1 to 30 carbon atoms or hydroxyalkyl groups containing from 1 to 30 carbons, Y is sulfate or sulfonate and x is an integer within the range of 1 to 10,000.

* * * * *